US012807918B2

(12) United States Patent
Richardson et al.

(10) Patent No.: US 12,807,918 B2
(45) Date of Patent: Nov. 24, 2026

(54) IN VITRO MYOCARDIAL TISSUE SCREENING DEVICES, SYSTEMS, AND METHODS

(71) Applicant: Clemson University Research Foundation, Clemson, SC (US)

(72) Inventors: William Richardson, Greenville, SC (US); Samuel Coeyman, Mt. Pleasant, SC (US); Jonathan G. Heywood, Central, SC (US); Michael J. Potter, Knoxville, TN (US)

(73) Assignee: Clemson University Research Foundation, Clemson, SC (US)

(*) Notice: Subject to any disclaimer, the term of this patent is extended or adjusted under 35 U.S.C. 154(b) by 917 days.

(21) Appl. No.: 17/895,567

(22) Filed: Aug. 25, 2022

(65) Prior Publication Data

US 2023/0064704 A1 Mar. 2, 2023

Related U.S. Application Data

(60) Provisional application No. 63/236,936, filed on Aug. 25, 2021.

(51) Int. Cl.
*C12M 3/00* (2006.01)
*C12M 1/32* (2006.01)
(Continued)

(52) U.S. Cl.
CPC ............ *C12M 41/46* (2013.01); *C12M 21/08* (2013.01); *C12M 23/12* (2013.01); *C12M 35/04* (2013.01); *G01N 33/5082* (2013.01)

(58) Field of Classification Search
None
See application file for complete search history.

(56) References Cited

U.S. PATENT DOCUMENTS

| | | | |
|---|---|---|---|
| 9,606,035 | B2 | 3/2017 | Williams et al. |
| 10,034,738 | B2 | 7/2018 | Thavandiran et al. |

(Continued)

FOREIGN PATENT DOCUMENTS

| | | | |
|---|---|---|---|
| EP | 2130904 | A2 | 12/2009 |
| EP | 3209340 | A0 | 6/2018 |

(Continued)

OTHER PUBLICATIONS

Raimondi et al., Development and biological validation of a cyclic stretch culture system for the ex vivo engineering of tendons, The International Journal of Artificial Organs, 2018, vol. 41(7) 400-412 (Year: 2018).*

(Continued)

*Primary Examiner* — Holly Kipouros
(74) *Attorney, Agent, or Firm* — Fredrikson & Byron, P.A.

(57) ABSTRACT

Various cardio tissue testing wells with an actuable attachment structure therein, and testing systems incorporating such wells therein. The various well embodiments can include an actuable attachment structure that is actuated by external energy, such as a magnetic field, fluidic pressure, or electrical actuation. The various system embodiments can
(Continued)

include a controller, a power source, and a testing plate containing a plurality of wells, wherein each well includes an actuable attachment structure.

20 Claims, 10 Drawing Sheets

(51) Int. Cl.
*C12M 1/34* (2006.01)
*C12M 1/42* (2006.01)
*G01N 33/50* (2006.01)

(56) References Cited

U.S. PATENT DOCUMENTS

| | | | | |
|---|---|---|---|---|
| 2004/0235153 | A1* | 11/2004 | Takagi | C12M 35/04 435/293.2 |
| 2014/0038258 | A1* | 2/2014 | Akra | C12M 35/02 435/297.1 |
| 2014/0113345 | A1 | 4/2014 | Lee et al. | |
| 2014/0273210 | A1 | 9/2014 | Baker et al. | |
| 2015/0313704 | A1 | 11/2015 | Thavandiran et al. | |
| 2017/0304500 | A1 | 10/2017 | Montgomery et al. | |
| 2017/0362560 | A1* | 12/2017 | Reich | C12M 23/20 |
| 2019/0029549 | A1* | 1/2019 | Sniadecki | A61B 5/243 |
| 2021/0253992 | A1* | 8/2021 | Jaiswal | C12M 23/38 |
| 2023/0357696 | A1* | 11/2023 | Christ | C12M 99/00 |
| 2024/0344022 | A1* | 10/2024 | Zenhausern | C12N 5/0062 |

FOREIGN PATENT DOCUMENTS

| | | | |
|---|---|---|---|
| WO | 2021094749 | A1 | 5/2021 |
| WO | 20210158233 | A1 | 8/2021 |
| WO | 20210158598 | A1 | 8/2021 |
| WO | 2022010594 | A1 | 1/2022 |

OTHER PUBLICATIONS

Flannery et al., 2017, Automated Uniaxial Tension System for Mechanically Active Tissue Culture, Worcester Polytechnic Institute (Year: 2017).*

"Electromagnetic Devices" FlexBooks 2.0. CK-12 Foundation, 22.5, 2022, https://flexbooks.ck12.org/cbook/ck-12-middle-school-physical-science-flexbook-2.0/section/22.5/primary/lesson/electromagnetic-devices-ms-ps/.

* cited by examiner

IN VITRO MYOCARDIAL TISSUE SCREENING DEVICES, SYSTEMS, AND METHODS

CROSS-REFERENCE TO RELATED APPLICATION(S)

This application claims the benefit under 35 U.S.C. § 119(e) to U.S. Provisional Application 63/236,936, filed Aug. 25, 2021 and entitled "In Vitro Myocardial Tissue Screening Systems," which is hereby incorporated herein by reference in its entirety.

FIELD

The various embodiments herein relate to in vitro tissue testing systems, and more specifically to in vitro myocardial tissue testing systems.

BACKGROUND

In vitro myocardial micro-tissue testing offers a low-cost, high-throughput approach to pre-screen many therapies prior to animal testing, and thereby select only those with the highest probability for efficacy and the lowest probability for unintended side effects. Certain known platforms test living, beating 3D myocardial micro-tissues in vitro. Using a platform for 3D culture of beating myocardial micro-tissues enables the simultaneous screening of different drug approaches and device interventions in order to identify the effects of those therapies on myocardial function, so poorly performing therapies can be screened out before wasting resources on animal testing. For therapies that perform well in vitro, the platform can be used to further optimize those specific formulations, time-courses, dosage combinations, etc. to enhance their performance for future animal and clinical trials. Additionally, in vitro cultures also enable personalized, patient-specific screens whereby each patient's own cells are used to build the micro-tissues for drug testing, enabling the identification of specific therapies that are optimized for that particular patient's genetic background.

One disadvantage of known in vitro myocardial tissue screening platforms is that they are constructed such that the beating micro-tissues contained therein simply transfer energy into their local attachments, which immediately transfer the same energy back into the micro-tissues.

There is a need in the art for improved in vitro myocardial tissue screening platforms.

BRIEF SUMMARY

Discussed herein are various cardio tissue testing wells with an actuable attachment structure therein, and related testing systems incorporating such wells.

In Example 1, a cardio tissue testing well comprises a chamber sized to receive a cardio tissue construct, a stationary tissue attachment structure disposed at a first end of the chamber, and an actuable tissue attachment structure disposed at a second end of the chamber.

Example 2 relates to the cardio tissue testing well according to Example 1, wherein the actuable tissue attachment structure comprises a magnet attached to the actuable tissue attachment structure.

Example 3 relates to the cardio tissue testing well according to Example 2, wherein the actuable tissue attachment structure comprises a slidable piston.

Example 4 relates to the cardio tissue testing well according to Example 3, wherein the slidable piston comprises a piston body and a body attachment structure.

Example 5 relates to the cardio tissue testing well according to Example 3, wherein the slidable piston is actuable by a magnetic field being applied to the magnet.

Example 6 relates to the cardio tissue testing well according to Example 1, wherein the actuable tissue attachment structure comprises a slidable piston.

Example 7 relates to the cardio tissue testing well according to Example 6, wherein the slidable piston is actuable by fluidic pressure being applied to the chamber.

Example 8 relates to the cardio tissue testing well according to Example 1, wherein the actuable tissue attachment structure comprises an electrically actuable material.

In Example 9, a cardio tissue testing system comprises a controller, an actuator operably coupled to the controller, and a culture plate operably coupled to the actuator, the culture plate comprising a plurality of microwells, the microwells comprising a chamber sized to receive a cardio tissue construct, a stationary tissue attachment structure disposed at a first end of the chamber, and an actuable tissue attachment structure disposed at a second end of the chamber, wherein the actuable tissue attachment structure is actuable to move away from and toward the stationary tissue attachment structure. The system further comprises an electrical power source operably coupled to the controller, wherein the electrical power source is operably coupled to electrodes associated with the culture plate, and a camera operably coupled to the controller, wherein the camera is positioned to be capable of capturing images of at least one of the microwells.

Example 10 relates to the cardio tissue testing system according to Example 9, wherein the actuator is an electromagnet.

Example 11 relates to the cardio tissue testing system according to Example 10, wherein the actuable tissue attachment structure comprises a magnet attached to the actuable tissue attachment structure.

Example 12 relates to the cardio tissue testing system according to Example 9, wherein the actuator is a plurality of fluidic reservoirs, wherein each of the fluidic reservoirs is fluidically coupled to one of the microwells.

Example 13 relates to the cardio tissue testing system according to Example 9, wherein the actuator is an electrical actuator operably coupled to the actuable tissue attachment structure in each of the plurality of microwells.

Example 14 relates to the cardio tissue testing system according to Example 13, wherein the actuable tissue attachment structure comprises an electrically actuable material comprising a dielectric polymer, a piezoelectric material, or a bimorph material.

In Example 15, a cardio tissue testing system comprises a controller, an electromagnet operably coupled to the controller, and a culture plate disposed adjacent to the electromagnet, the culture plate comprising a plurality of microwells, the microwells comprising a chamber sized to receive a cardio tissue construct, a stationary tissue attachment structure disposed at a first end of the chamber, an actuable piston disposed at a second end of the chamber, the actuable piston comprising a magnet and a piston attachment structure, wherein the actuable piston is actuable to move away from and toward the stationary tissue attachment structure, and electrodes associated with the culture plate. The system further comprises an electrical power source operably coupled to the controller and the electrodes, and a camera operably coupled to the controller, wherein the camera is positioned to be capable of capturing images of at least one of the microwells.

Example 16 relates to the cardio tissue testing system according to Example 15, wherein the controller is configured to be capable of actuating the electromagnet to apply a magnetic field to the culture plate, whereby each of the actuable pistons is actuated to be urged either away from or toward the stationary tissue attachment structure.

Example 17 relates to the cardio tissue testing system according to Example 16, wherein the actuation of the electromagnet to actuate the actuable pistons is configured to be capable of subjecting a cardiac tissue disposed within each of the microwells to a full cardiac cycle.

Example 18 relates to the cardio tissue testing system according to Example 15, wherein the culture plate comprises 32 microwells.

Example 19 relates to the cardio tissue testing system according to Example 15, wherein the actuable piston comprises a piston body, wherein the piston attachment structure and the magnet are attached to the piston body.

While multiple embodiments are disclosed, still other embodiments will become apparent to those skilled in the art from the following detailed description, which shows and describes illustrative embodiments. As will be realized, the various implementations are capable of modifications in various obvious aspects, all without departing from the spirit and scope thereof. Accordingly, the drawings and detailed description are to be regarded as illustrative in nature and not restrictive.

BRIEF DESCRIPTION OF THE DRAWINGS

FIGS. 12A-23E are top views of various flow restriction components, according to one embodiment.

DETAILED DESCRIPTION

Disclosed herein are various embodiments of an in vitro tissue culture platform or system that replicates the in vivo environment for myocardial tissue by enabling control over the mechanical loading environment of myocardial tissue samples for the purpose of experimental disease, drug, and device screens. While known platforms can electrically stimulate tissues to contract as described above, the tissues in those known platforms are attached to non-actuable attachment structures, thereby resulting in the in vitro tissues being subjected to unnatural stress and strain. In contrast, as will be described in detail below, the various system implementations herein have actuable attachment structures such that the systems can subject the tissues disposed therein to a full cardiac cycle akin to in vivo pressure-volume relationships in which the tissues undergo isometric contraction, shortening, isometric relaxation, and lengthening.

Figure 1A:
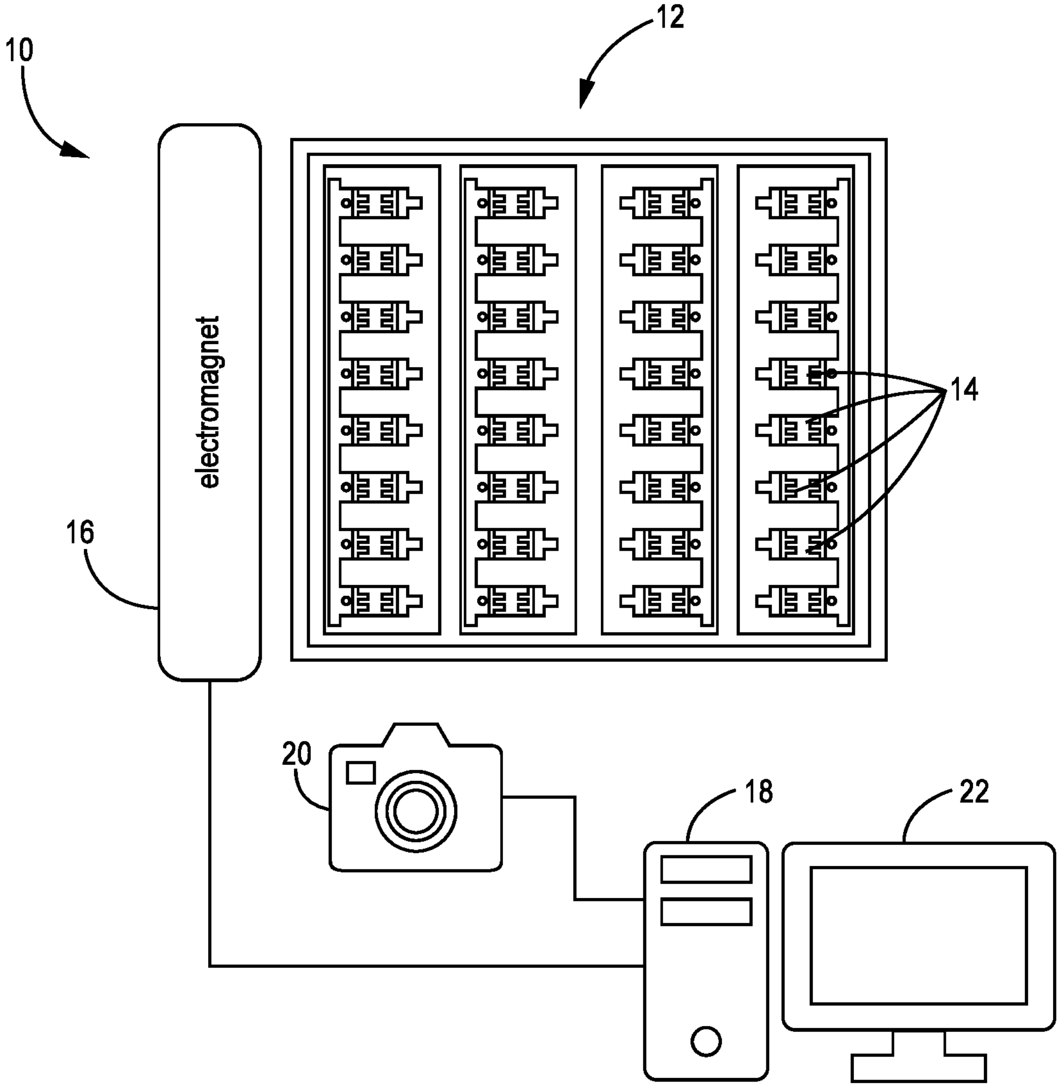
FIG. 1A is a schematic depiction of a cardio tissue testing system, according to one embodiment.
Figure 1B:
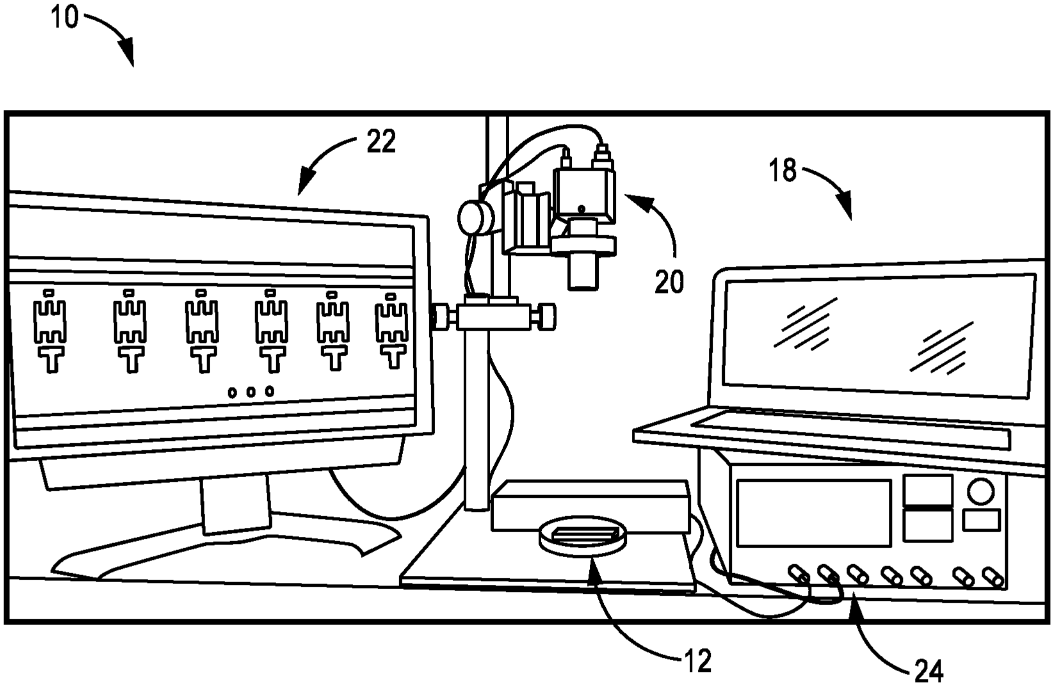
FIG. 1B is a view of the components of the cardio tissue testing system of claim 1A, according to one embodiment.

One exemplary system embodiment 10 is depicted in FIGS. 1A and 1B, with FIG. 1A providing a schematic depiction of the various system 10 components and FIG. 1B depicting an exemplary system 10 setup. This specific system 10 utilizes electromagnetic actuation as described in detail below. The electromagnetic actuation system 10 has a culture plate 12 containing multiple wells 14, an electromagnet 16 disposed adjacent to the plate 12, a processor/controller 18 coupled to the electromagnet 16, a camera/viewer 20 coupled to the controller 18, a monitor 22 coupled to the controller 18, and a power source 24 coupled to the controller 18 and the other components.

As noted above, the culture plate 12 has multiple small culture wells 14. According to certain embodiments, the culture plate 12 is a 32-well plate 12. Alternatively, the plate 12 can have 6, 12, 24, 48, 96, 384, or 1,536 wells 14. In a further alternative, the plate 12 can have any known number of wells 14. Alternatively, the plate 12 can be any known square culture plate 12 with the desired number of wells 14. Further, the plate 12 can be made of polystyrene, PEEK, Lexan polycarbonate, or any other known biocompatible rigid plastic or polymeric material. In use, living, beating myocardial tissue constructs (such as the tissue 62 depicted in FIG. 3B, for example) are positioned in the wells 14 such that the constructs (such as constructs 62) are subjected to the full cardiac cycle for various testing purposes.

As noted above, an electromagnet 16 can be positioned adjacent to the culture plate 12 as shown in FIG. 1A. For a culture plate 12 with 32 wells, the electromagnet 16 can be an electromagnet with a wattage of 52W from McMaster-Carr (catalog #5684K23). Alternatively, the electromagnet can be any known electromagnet with sufficient strength to apply a sufficient magnetic field to move the actuable pistons 66 in the wells 44 as discussed below. Thus, the larger the culture plate 12 (the greater the number of wells 44), the larger the electromagnet required to actuate the pistons 66 in those wells 44, and vice versa. In accordance with certain embodiments, the electromagnet 16 is placed in contact or near contact with the culture plate 12. Alternatively, the electromagnet 16 can be placed within about two inches of the plate 12.

In accordance with certain implementations as discussed in additional detail below, the electromagnet 16 operates to apply a magnetic field to the wells 44 in the plate 12, thereby actuating the piston 66 in each well 44 to move. More specifically, the controller 18 is coupled to the electromagnet 16 and actuates the electromagnet 16 to urge the pistons 66 to move in a predetermined fashion in each well 44 as detailed below.

In one embodiment, the camera 20 is a Hayear 14MP HDMI Microscope Camera. Alternatively, the camera 20 can be any known camera or imager for use in labs and/or with microscopes. In certain implementations, the camera 20 can capture images at a rate of at least 30 frames per second to fully capture the cardiac tissue dynamics. In the various system embodiments herein (including system 10), the camera 20 is coupled to the controller 18 such that the controller 18 can be used to operate the camera 20 to capture images of the tissue constructs in each well 44 within the plate 12.

Figure 2A:
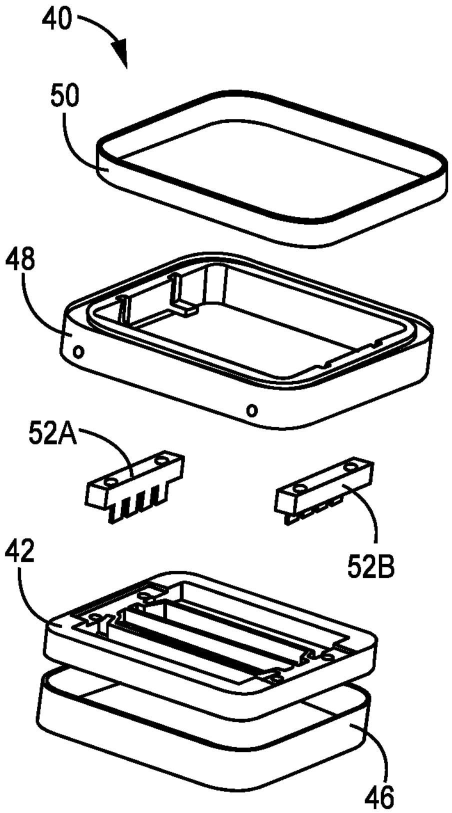
FIG. 2A is an exploded perspective view of a culture plate with 32 wells, according to one embodiment.
Figure 2B:
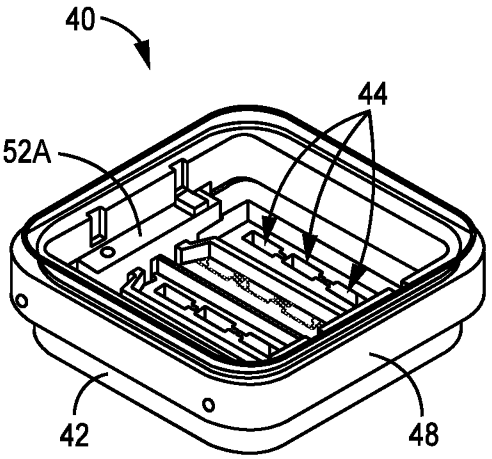
FIG. 2B is a perspective view of the culture plate of FIG. 2A, according to one embodiment.

One exemplary culture plate 40 is depicted in FIGS. 2A and 2B, according to one embodiment. The plate 40 has a well base 42 that contains multiple wells 44, a plate base 46 to which the well base 42 is coupled, sidewalls 48, a well lid (or cap) 50, and electrodes 52A, 52B disposed on each side of the well base 42 as shown. According to various implementations, the plate base 46 and the well lid (or cap) 50 are the bottom and top components of a petri dish commercially available from Electron Microscopy Sciences (catalog #70690) that allow for visualization of the wells 44 through the transparent lid 50. In such embodiments, the well base 42 and sidewalls 48 are sized to fit within the petri dish. Each electrode 52A, 52B can have a separate wire (not shown) coupled thereto such that the wire provides electrical current to that electrode 52A, 52B. More specifically, the separate wires (not shown) are coupled to an external power supply that is coupled to the controller 18 such that the controller 18 can modulate the electrical current to deliver voltage pulses into the culture media (liquid) disposed within the plate 40 via the electrodes 52A, 52B. One of the electrodes 52A, 52B is positive and the other 52A, 52B is negative, thereby producing a voltage differential across the plate 40 that induces an electrical current flowing across the tissue in each well 44, thereby stimulating cardiomyocyte cell contraction. In one embodiment, the well base 42, the wells 44 therein, and the sidewalls 48 can be 3D printed and thus can be made of commercially-available biocompatible resin. Further, in various implementations, instead of using the petri dish components as described above, the plate base 46, and well lid 50 can be 3D printed as well. Alternatively, the base 42, sidewalls 48, plate base 46, and well lid 50 can be made of any known biocompatible material (such as polystyrene, polycarbonate, PEEK, glass, etc.). In a further alternative, as mentioned above, any known, commercially available culture plate for cardiac tissue with a desired amount of wells with appropriate incorporation of the actuable components as described herein can be used with the various system embodiments herein.

Figure 3A:
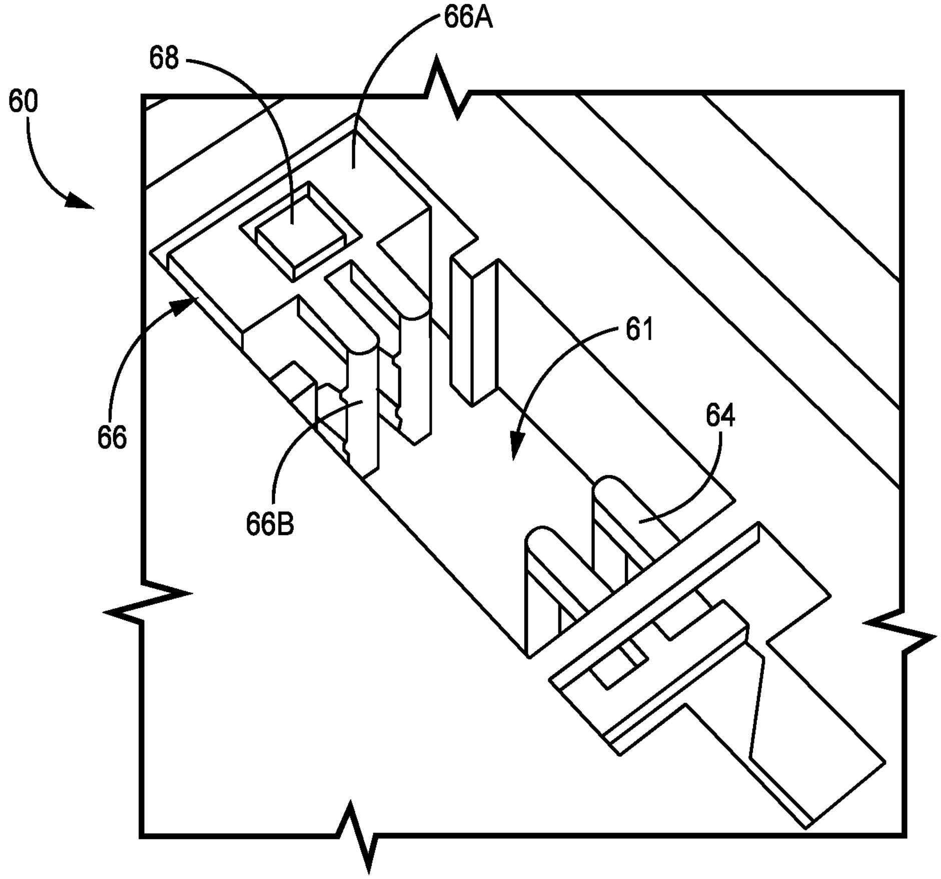
FIG. 3A is a perspective view of a well, according to one embodiment.
Figure 3B:
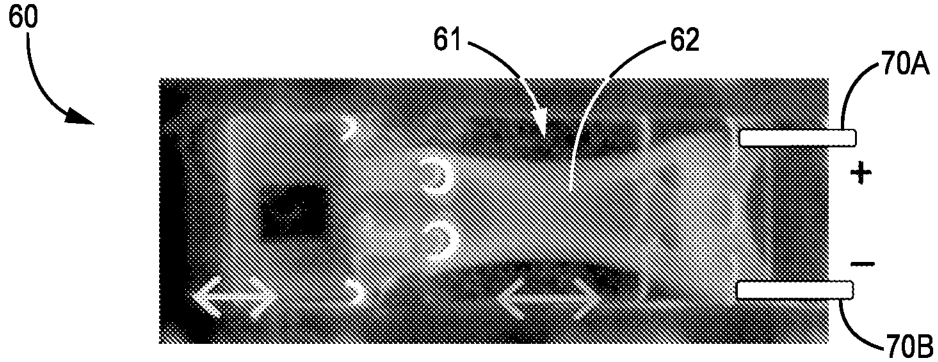
FIG. 3B is a top view of the well of FIG. 3A, according to one embodiment.

An exemplary well 60 (disposed on or formed in a plate such as plate 40) is depicted in FIGS. 3A and 3B, according to one embodiment, with FIG. 3A depicting a perspective view and FIG. 3B depicting a top cross-sectional view. The well 60 has a chamber 61 in which the tissue construct 62 can be disposed, as best shown in FIG. 3B. In one embodiment, the chamber 61 has a length of about 11 mm, a width of about 4 mm, and a depth of about 3.2 mm. Alternatively, the length can range from about 1 mm to about 22 mm, the width can range from about 0.2 mm to about 8 mm, and the depth can range from about 0.2 mm to about 8 mm. The chamber 61 also can contain a liquid (the culture medium, which is not shown) such that the tissue construct 62 is disposed within the culture medium (not shown) within the chamber 61. In one embodiment, the culture medium is a standard tissue culture medium that is comprised of DMEM+10% Horse Serum+33 ug/mL Aprotinin+10 ug/mL Insulin+50 ug/mL L-Ascorbic Acid+1% antibiotic/antimycotic. Alternatively, the various components therein can be used in different amounts and/or replaced with similar components. In a further alternative, the culture medium can be any known tissue culture medium.

In accordance with one embodiment as shown, the well 60 has a stationary attachment structure (or "stationary grip") 64 at one end of the chamber 61 and a slidable attachment structure (or "piston") 66 slidably disposed at the other end of the chamber 61. As such, a tissue construct 62 can be placed within the chamber 61 and coupled at one end to the stationary attachment structure 64 and at the other end to the piston 66. In one embodiment, the piston 66 has a piston body 66A with a magnet 68 attached thereto, along with a body attachment structure (or "piston grip") 66B coupled to the piston body 66A. The piston 66 is slidable along the length of the chamber 61 in response to a magnetic field being applied on the magnet 68 and/or force being applied by the construct 62.

As shown, the stationary attachment structure 64 and the body attachment structure 66B are both two attachment posts 64, 66B as shown. Alternatively, the attachment structures 64, 66B can be any known attachment structures for 3D tissue cultures, including any post- or pillar-based designs. For example, the structures 64, 66B could be one or more pillars/posts. Further, the structures 64, 66B could of various cross-sectional sizes and shapes (including square vs. cylindrical), etc. The magnet 68 can be a permanent magnet 68 with a size ranging from about 0.25 mm to about 5 mm. For example, the magnet 68 is a rare earth neodymium cube magnet which is commercially available from supermagnetman.com. Alternatively, the magnet 68 can be any known permanent and/or rare earth magnet of the appropriate size.

Stimulation electrodes 70A, 70B are shown schematically in FIG. 3B because, like the electrodes 52A, 52B discussed above, these electrodes 70A, 70B are electrically coupled to each well, including exemplary well 60 as shown, and in electrical communication with the chamber 61. As such, the electrodes 70A, 70B can be used to apply electrical charges to the medium (not shown) within the chamber 61, thereby applying electrical charges to the tissue construct 62. Thus, the electrodes 70A, 70B can be used to actuate the tissue construct 62 to contract and relax in a fashion that replicates in vivo myocardial tissue.

In accordance with one embodiment, the system 10 can be operated in the following manner. After tissue constructs (such as construct 62) are placed in the wells 14 (or wells 44 or 60) of the culture plate 12 (or plate 40), the controller 18 can be used to replicate the full cardiac cycle for each of the constructs in each well, subjecting each tissue to the contraction, shortening, isometric relaxation, and lengthening steps. More specifically, the controller 18 can actuate the electromagnet 16 to apply a magnetic field to each magnet (such as magnet 68) on each piston (such as piston 66) in each well (such as well 14, 44, or 60), thereby urging each piston to move in relation to the construct 62 as needed for each relevant step of the cycle. At the same time, the controller 18 can also actuate the stimulation electrodes (such as electrodes 70A, 70B) to actuate the tissue construct 62 as needed for each relevant step of the cycle.

Figure 4A:
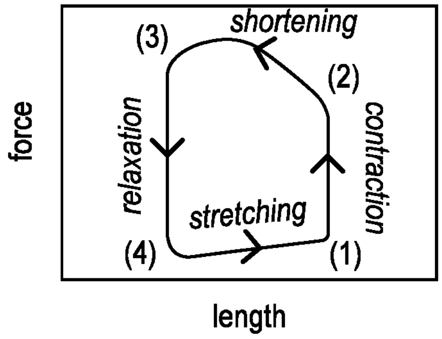
FIG. 4A is a graphical representation of the cardiac cycle, according to one embodiment.
Figure 4B:
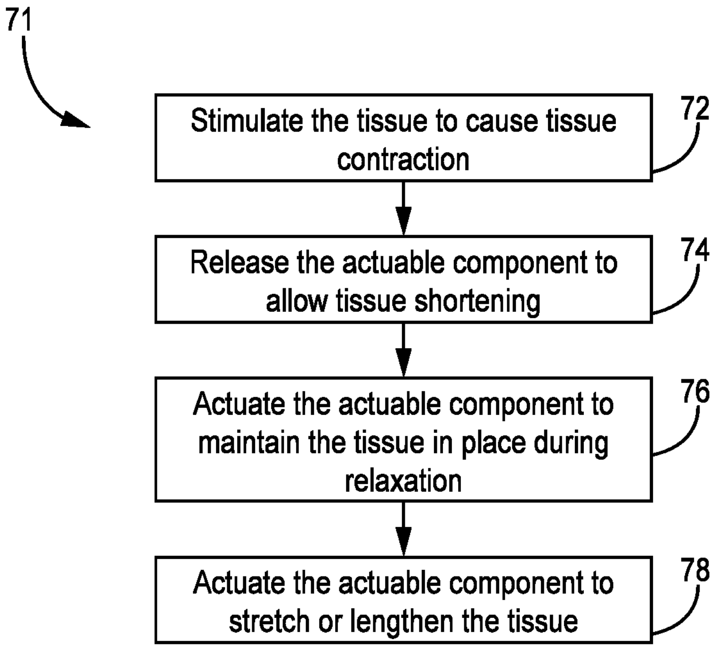
FIG. 4B is a method of simulating the cardiac cycle for a tissue construct, according to one embodiment.

By appropriately controlling the magnetic and contractile forces via the controller 18, the system 10 (and the other system embodiments herein) can control the dynamic force-length relationship for each construct 62 in each well (such as well 14, 44, or 60) to represent the pressure-volume mechanical relationship of the heart in vivo, which is depicted graphically in FIG. 4A. That is, the system 10 (and other system embodiments) can be used to control the actuable component in each well (which is the actuable piston 66 in this specific embodiment) as shown in the method embodiment 71 set forth in FIG. 4B to simulate the cardiac cycle for each construct. Specifically, the controller 18 can cause electrical stimulation of the tissue 62 in each well 14, 44, 60 (by the electrodes 70A, 70B) to drive tissue force generation while also controlling the pistons 66 in each well 14, 44, 60 magnetically (by the electromagnet 16) to prevent tissue deformation (isometric contraction phase) (block 72). Next, the controller 18 releases the magnetic resistance (by the electromagnet 16) to enable shortening by the muscle contractile forces (shortening phase) (block 74), after which the controller 18 again applies magnetic control (via the electromagnet 16) to hold the tissue 62 in each well 14, 44, 60 in place while the muscle relaxes (isometric relaxation phase) (block 76). Finally, the controller 18 applies magnetic control (via the electromagnet 16) to stretch the tissue 62 back out (lengthening or "stretching" phase) (block 78). This cardiac cycle simulation is also achieved in substantially the same way in the other system embodiments disclosed or contemplated herein, as described in additional detail below.

Figure 6:
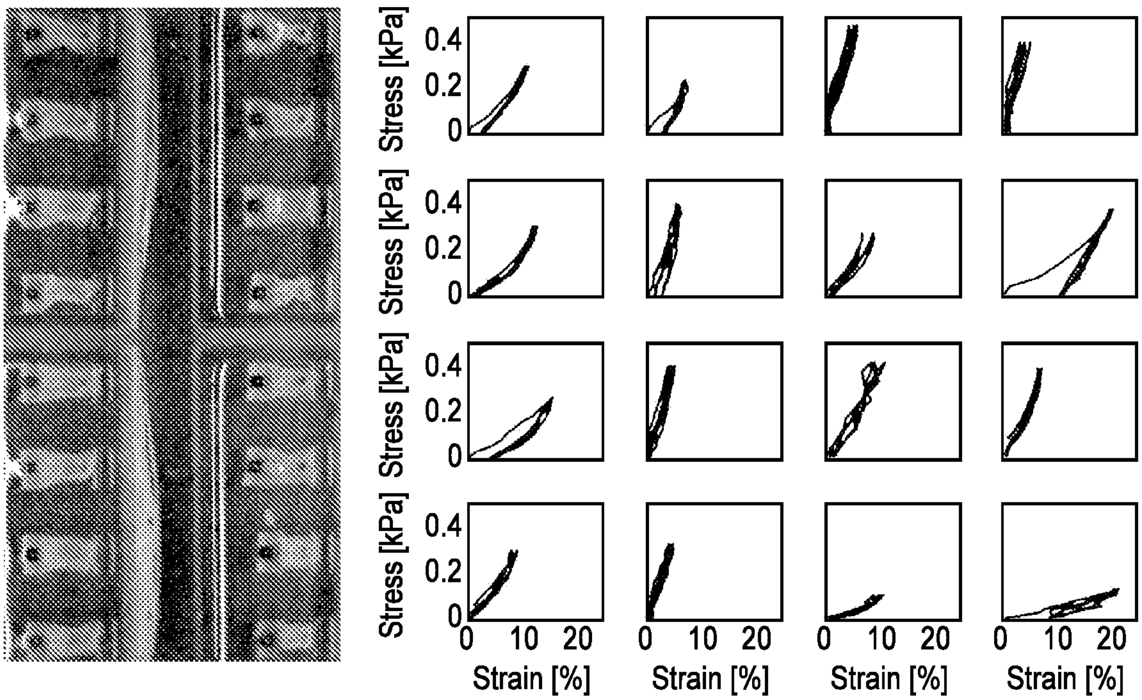
FIG. 6 is an image and graphical representation of mechanical property characterization tests being performed on cardiac tissues, according to one embodiment.

In alternative embodiments, the system 10 can also be used for other purposes. For example, in one exemplary implementation, the controller 18 can be used to actuate the electromagnet 16 to perform multiplex mechanical property characterization tests by tracking tissue deformation under known forces (e.g., stiffness moduli from stress-strain plots). An exemplary graphical summary of such tests is depicted in FIG. 6, which shows the impact on individual tissue constructs in individual wells of applying strain forces to the constructs without any electrical stimulation thereof.

According to a further system 80 embodiment as shown in FIGS. 7-9B, the system 80 is a fluidically actuated system 80 (instead of the electromagnetic actuation of the system 10 described above). Except as described in detail below, the system 80 can have the same or substantially similar components that operate in substantially the same way as the components of the system 10 above, including the culture plate 12, the controller 18, the camera 20, the monitor 22, and the power source 24 of the system 10, regardless of whether such components are depicted or discussed in relation to the system 80.

Figure 7:
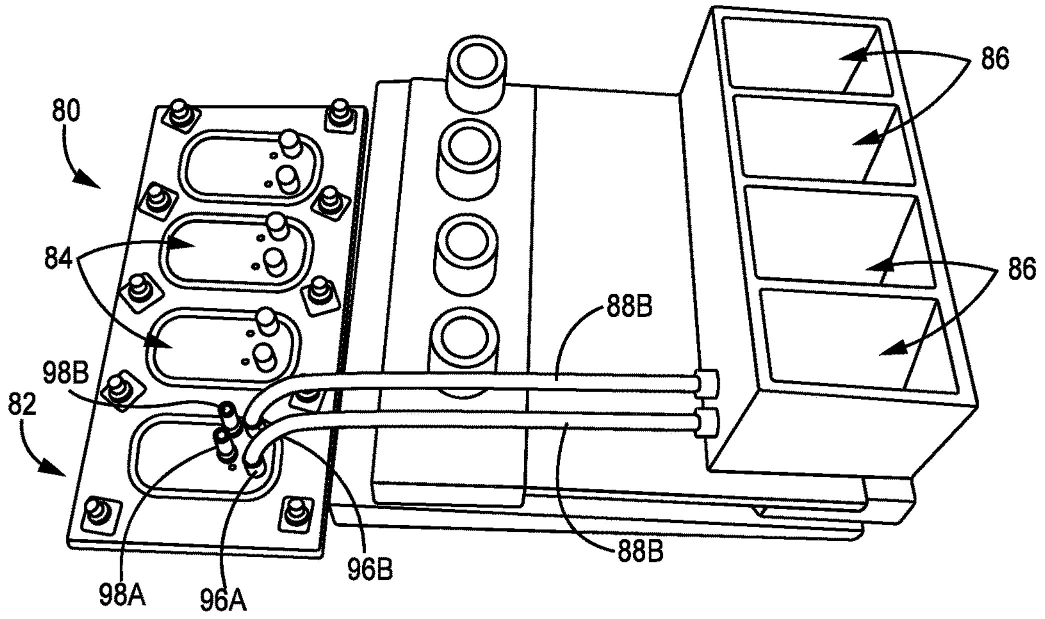
FIG. 7 is a perspective view of another cardio tissue testing system, according to a further embodiment.
Figure 8A:
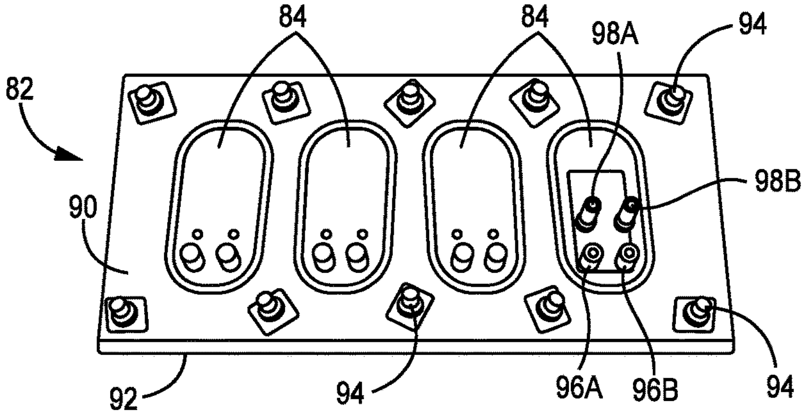
FIG. 8A is a top view of an illustrative culture plate for use with the system of FIG. 7, according to one embodiment.
Figure 8B:
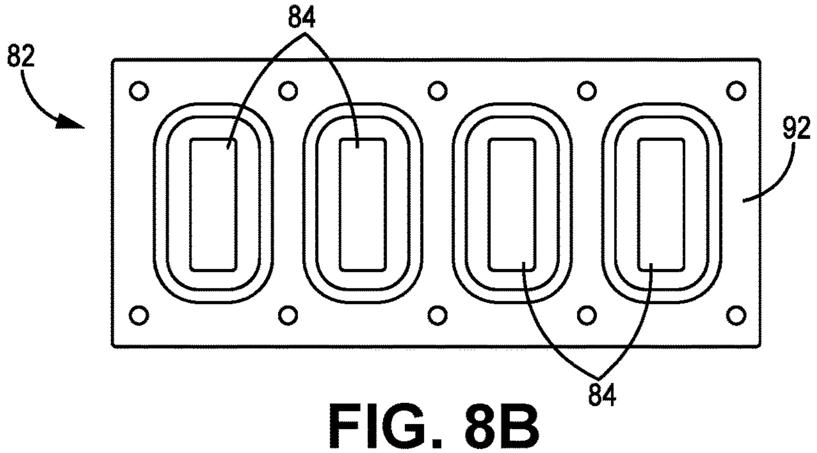
FIG. 8B is a top view of the culture plate of FIG. 8A with the top plate removed, according to one embodiment.

As best shown in FIGS. 7-8B, this system 80 embodiment includes a culture plate 82 in which each of the multiple wells 84 are fluidically coupled to a separate reservoir 86 via fluidic channels 88A, 88B. While the figures depict an illustrative plate 82 having only four wells 84, it is understood that the plate 82 (and the number of wells 84) as depicted is provided solely for demonstrative purposes and does not necessarily reflect the actual size of the plates 82 to be used within the system 80. Thus, the various plates 82 used with this system 80 can have the same number of wells 84 as the plates 12, 40 discussed above with respect to system 10. FIGS. 8A and 8B depict an expanded view of the plate 82. More specifically, FIG. 8A shows the plate 82 with the top component 90 disposed on the plate 82 (with the top component 90 coupled to the bottom component 92 via the attachment mechanisms 94), while FIG. 8B depicts the plate 82 without the top component 90, thereby showing the bottom component 92 and the interior of the wells 84 defined within the bottom component 92. The top 90 and bottom 92 components can be 3D printed and thus can be made of commercially-available biocompatible resin. Alternatively, the components 90, 92 can be made of any known rigid biocompatible material (such as polystyrene, polycarbonate, PEEK, glass, etc.). The attachment mechanisms 94 as shown are nuts and bolts 94. Alternatively, any known mechanisms or methods for attachment of the bottom component 92 and the top component 90 can be used. In this embodiment, the top component 90 includes entry and exit valves 96A, 96B and the stimulation electrodes 98A, 98B for each of the wells 84 as shown. Alternatively, the valves 96A, 96B and electrodes 98A, 98B for each well 84 can be attached to and extend through the bottom component 92.

As best shown in FIG. 8B, each well 84 is defined in the bottom component 92 by a fluidic seal component 85 as shown. More specifically, the fluidic seal component 85 can be a flexible border 85 that fluidically seals the well 84 when the top component 90 is attached to the bottom component 92. Alternatively, any known fluidic seal component 85 can be used.

Figure 9:
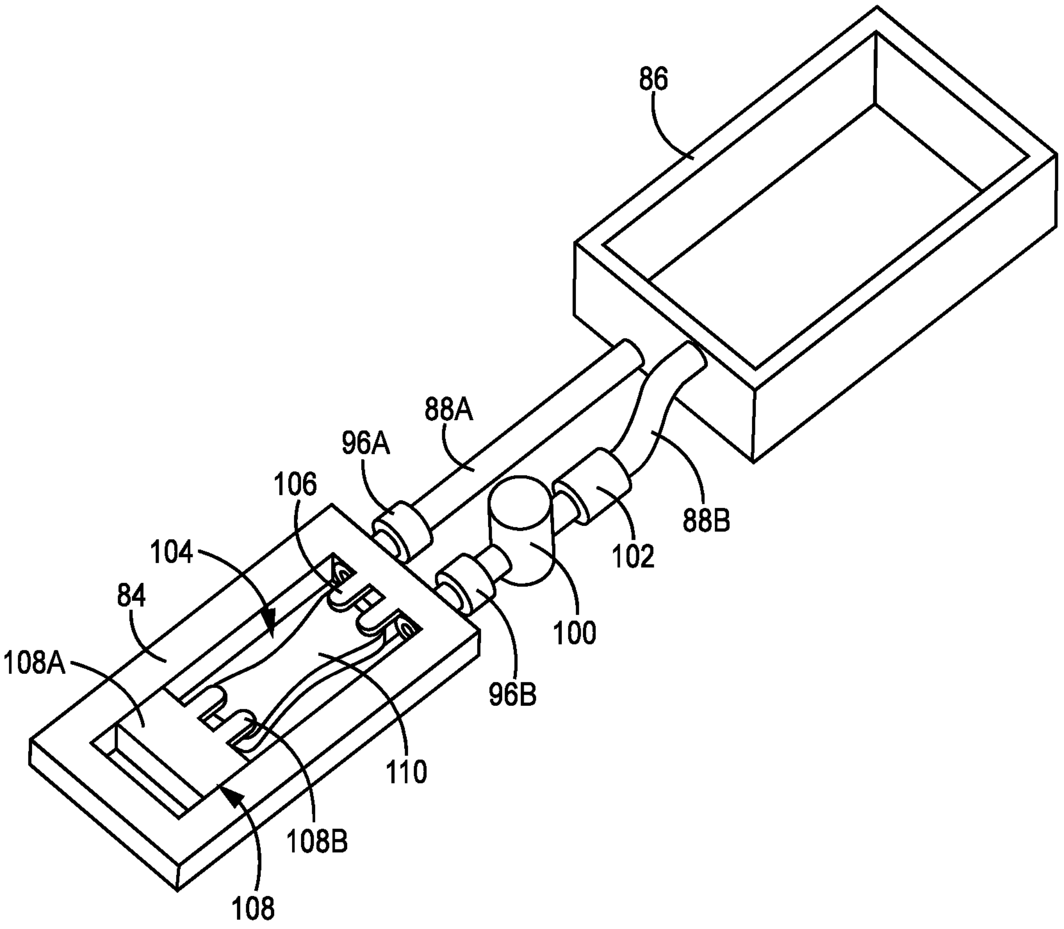
FIG. 9 is a perspective view of a single circulation loop of another cardio tissue testing system, according to another embodiment.

FIG. 9 provides a schematic depiction of one embodiment of a single well 84 coupled to its associated reservoir 86. As noted above, the well 84 is fluidically coupled to the reservoir 86 via the fluidic channels 88A, 88B, with the channel 88A being the entry channel 88A and the channel 88B being the exit channel 88B, to form a circulation loop that is fluidically sealed such that the pressure in the well 84 is directly related to the pressure in the reservoir 86. The entry channel 88A is coupled to the well 84 at the entry valve 96A, while the exit channel 88B is coupled to the well 84 at the exit valve 96B. In certain embodiments, the entry and exit valves 96A, 96B are one-way, pressure sensitive valves 96A, 96B that only allow liquid to pass through the valves 96A, 96B upon achieving a minimum pressure and only in one direction. Alternatively, any known valve mechanisms can be used.

Figure 10A:
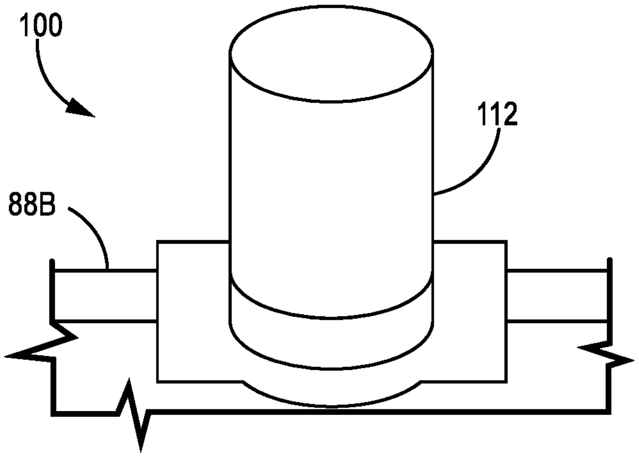
FIG. 10A is a perspective view of a capacitance component, according to one embodiment.
Figure 10B:
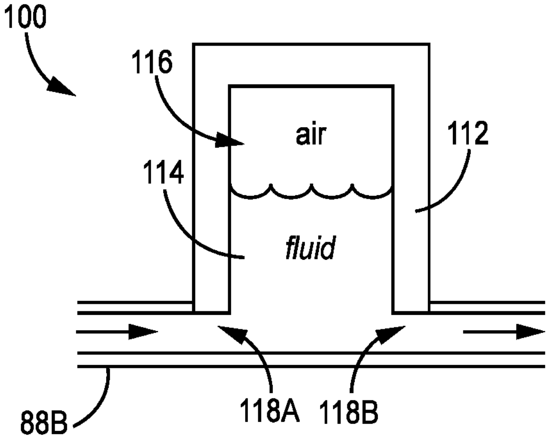
FIG. 10B is a schematic cross-sectional view of the capacitance component of FIG. 10A, according to one embodiment.

The exit channel 88B in this implementation has a capacitance component 100 and a resistance component 102 disposed along the length of the channel 88B. In one embodiment, the capacitance component 100 is provided to replicate or simulate the arterial compliance that occurs in vivo, as described in detail below. For example, according to certain implementations as shown in FIGS. 10A and 10B, the capacitor 100 can have a body 112 with an inner chamber 114 in fluidic communication with the exit channel 88B as shown. The inner chamber XX contains a pocket of air 116 disposed within the chamber 114 and an inlet 118A and outlet 118B in communication with the chamber 114 and the exit channel 88B such that the media can pass through the chamber 114 and out of the device 100. The pocket 116 can be made up of any type of gas, but typically is captured ambient air. As the culture media enters the capacitor 100 via the exit channel 88B, the pocket of trapped air within the chamber 114 is compressed in a fashion similar to the compliance of an artery that would occur as blood is exiting the heart in vivo.

According to certain implementations, the capacitor 100 can be 3D printed and thus can be made of commercially-available biocompatible resin. Alternatively, the capacitance component 100 can be made with any known methods and of any known materials with appropriate characteristics. In a further alternative, the capacitance component 100 can be any known capacitance device or other similar device that can simulate artery compliance.

Figure 11:
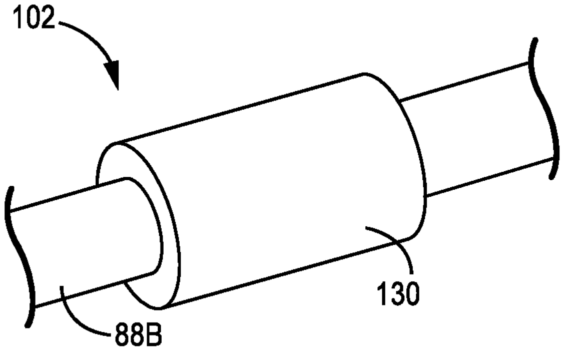
FIG. 11 is a perspective view of a resistance component, according to one embodiment.
Figure 12A:
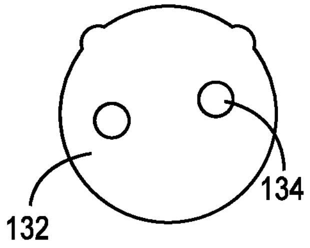
Figure 12B:
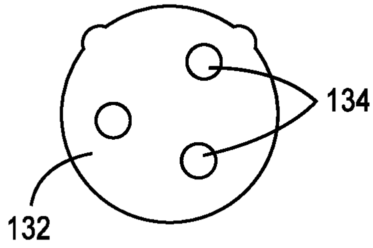
Figure 12C:
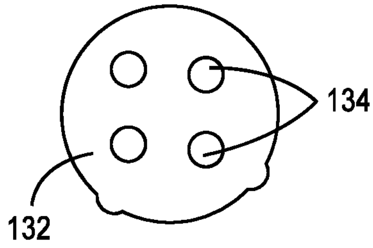
Figure 12D:
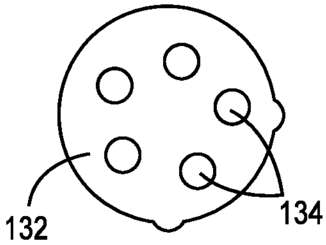
Figure 12E:
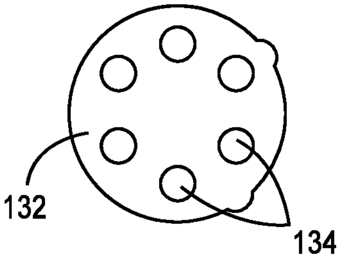

Further, according to one implementation, the resistance component 102 as shown in FIGS. 11-12E is provided to replicate or simulate the resistance of blood flow through an in vivo capillary bed, as also described in detail below. In one embodiment, the resistor 102 has a resistor body 130 that receives the exit channel 88B as shown. Disposed within the resistor body 130 is a flow restriction body 132 that has at least one small opening or channel 134 defined therethrough such that the media flowing through the exit channel 88B and into the resistor 102 must pass through the one or more openings 134.

As shown in FIGS. 12A-12E, any one of several interchangeable flow restriction bodies 132 (or interchangeable resistance components 102 containing such bodies 132) with varying levels of flow restriction can be disposed within the resistor body 130. The various exemplary restriction bodies 132 as shown have two openings 134 as shown in FIG. 12A, three openings 134 as shown in FIG. 12B, four openings 134 (FIG. 12C), five openings 134 (FIG. 12D), and six openings 134 (FIG. 12E). The flow restriction bodies 132 depicted in FIGS. 12A-12E are exemplary and non-limiting. In other words, the flow restriction body 132 can also have one opening, seven openings, eight openings, nine openings, ten openings, or any other number of openings.

The openings or channels 134 create fluidic resistance as the media passes through. One opening 134 provides the most flow restriction, while each additional opening 134 lessens the flow restriction by predetermined amounts. As such, the amount of flow restriction can be controlled by the selection of any one of the different restriction bodies 132 as depicted or contemplated herein. In certain implementations, in addition to the number of channels 134 being adjusted/adjustable/interchangeable as discussed above, the channels 134 can also be modified with respect channel radius and/or channel length to further adjust the amount of fluidic resistance applied to the media as it passes through.

According to certain implementations, the resistance component 102 can be 3D printed and thus can be made of commercially-available biocompatible resin. Alternatively, the resistance component 102 can be made with any known methods and of any known materials with appropriate characteristics. In a further alternative, the resistance component 102 can be any known flow resistance device or mechanism for simulating blood flow resistance.

In this exemplary implementation, the well 84 has a chamber 104 with a stationary attachment structure (or "stationary grip") 106 at one end of the chamber 104 and a slidable attachment structure (or "piston") 108 slidably disposed at the other end of the chamber 104. As such, a tissue construct 110 can be placed within the chamber 104 and coupled at one end to the stationary grip 106 and at the other end to the piston 108. In one embodiment, the piston 108 has a piston body 108A and a body attachment structure (or "piston grip") 108B coupled to the piston body 108A. The piston 108 is slidable along the length of the chamber 104 in response to fluidic pressure being applied by fluid from the reservoir 86 and/or force being applied by the construct 110.

This system 80 operates in a fashion similar to the system 10 discussed above by replicating the full cardiac cycle for the tissue constructs 110 disposed within the wells 84, in this case via fluidic actuation instead of electromagnetic actuation. That is, by appropriately controlling the fluidic and contractile forces via the controller 18 (as shown in FIGS. 1A and 1B with respect to system 10), the dynamic force-length relationship can be controlled for each construct 110 in each well 84 to represent the pressure-volume mechanical relationship of the heart in vivo (as depicted graphically in FIG. 4, which is also discussed above). More specifically, the controller (such as controller 18) can cause electrical stimulation of the tissue 110 in each well 84 (by the electrodes 98A, 98B) to drive tissue force generation. In other words, the stimulation causes the tissue 110 to contract, which pulls the piston 108 toward the tissue 110, thereby increasing fluid pressure within the culture chamber 104 (isometric contraction phase). As a result of the fluidic coupling of the well 84 and the reservoir 86, this increased pressure causes some of the culture media to be ejected out of the chamber 104 through the exit valve 96B and into the reservoir 86 (shortening phase). The tissue 110 then relaxes in place (isometric relaxation phase). At this point, the increased pressure of the culture media being urged into the chamber 104 during the shortening phase causes culture media to be urged back into the chamber 104 from the reservoir 86 via the entry channel 88A and the entry valve 96A, which urges the piston 108 away from the tissue 110, thereby causing the tissue 110 to stretch back out (lengthening phase).

During the contraction phase, when the culture media exits the well 84, it passes through the capacitance component 100 to simulate arterial compliance and through the resistance component 102 to similar blood flow resistance, as described in further detail above. Thus, the various system 80 embodiments herein can include a capacitor 100 that can be modified to control the simulation of the arterial compliance and further can include a resistor 102 that can be modified to control the simulation of the blood flow resistance.

Alternatively, the system 80 can have a fluidic pump and related sensors incorporated into the system and coupled to the controller 18 such that the culture media can be urged into and out of the well 84 in a fashion similar to that described above. As such, the controller 18 and pump (not shown) could be used to create more precise control of the pressures within the well 84 and the reservoir 86 and thereby control the piston 108 with additional precision as well.

In alternative embodiments, the system 80 can also be used for other purposes. For example, in one exemplary implementation, the controller 18 can be used to actuate the fluidic system to perform multiplex mechanical property characterization tests by tracking tissue deformation under known forces (e.g., stiffness moduli from stress-strain plots). As noted above, an exemplary graphical summary of such tests is depicted in FIG. 6.

According to a further system 140 embodiment as shown in FIGS. 13A-13D, the system 140 is an electrically actuated system 140 (instead of the electromagnetic or fluidic actuation of the systems 10, 80 described above). While FIGS.

13A-13D depict solely an exemplary well 142, it is understood that the rest of the system components can be substantially similar to the components of system 10 as described in detail above. That is, except as described in detail below, the system 140 can have the same or substantially similar components that operate in substantially the same way as the components of the system 10 above, including the culture plate 12, the controller 18, the camera 20, the monitor 22, and the power source 24 of the system 10, regardless of whether such components are depicted or discussed in relation to the system 140.

In this exemplary implementation, the well 142 has a stationary attachment structure (or "stationary pillar") 144 at one end of the well 142 and an actuable attachment structure (or "actuable pillar") 146 slidably disposed at the other end of the well 142. As such, a tissue construct 148 can be placed within the well 142 and coupled at one end to the stationary pillar 144 and at the other end to the actuable pillar 146. In one embodiment, the actuable pillar 146 is made of an actuable material, such as any known dielectric polymer, piezoelectric, or bimorph material such that electrical actuation of pillar 146 can cause directed movement of the pillar 146 (as represented for example by the arrows A in FIG. 13A). Alternatively, the actuable pillar 146 can be made of a pliable, deformable material that has one or more electrically actuable components (not shown) associated with or disposed within the actuable pillar 146. For example, in one embodiment, the electrically actuable pillar 146 is a bimorph cantilever. Alternatively, the actuable pillar 146 is made of a dielectric material. In a further alternative, the electrically actuable pillar 146 can be made of any known electrically actuable material such that electrical energy can trigger the pillar 146 to move in a predetermined manner. Thus, the controlled deformations of the actuable pillar 146 can be controlled by electrical energy provided by the controller (such as controller 18 discussed above) to the pillar 146 via an electrical coupling such as a wire (not shown) or the like. More specifically, the actuable pillar 146 is movable toward and away from the tissue construct 148 in response to electrical energy provided by the controller (such as controller 18) and/or force being applied by the construct 148.

Figure 13A:
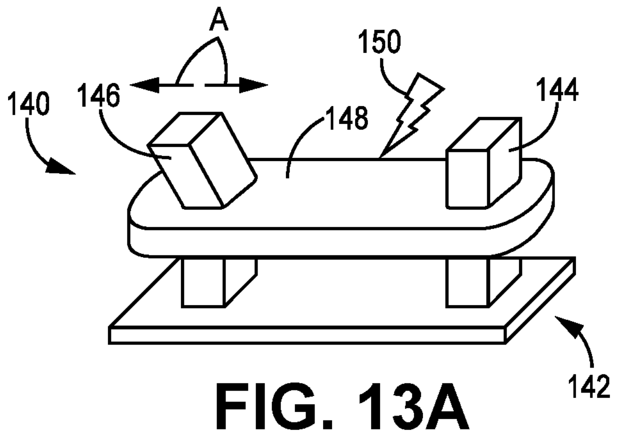
FIG. 13A is a schematic perspective view of the components of an exemplary well in another cardio tissue testing system in which the actuable pillar is being actuated to move in the contraction phase of the cardiac cycle, according to an additional embodiment.
Figure 13B:
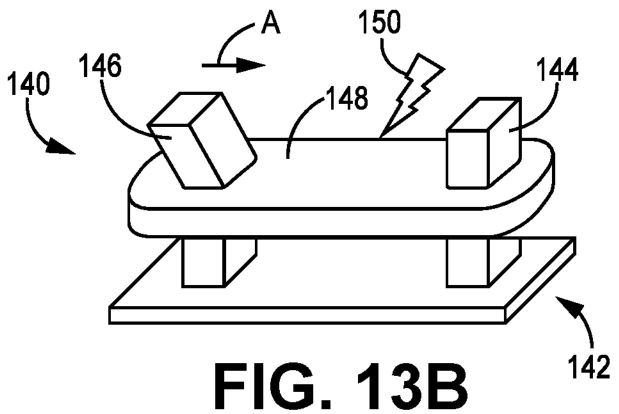
FIG. 13B is a schematic perspective view of the exemplary well of FIG. 13A in the shortening phase, according to one embodiment.
Figure 13C:
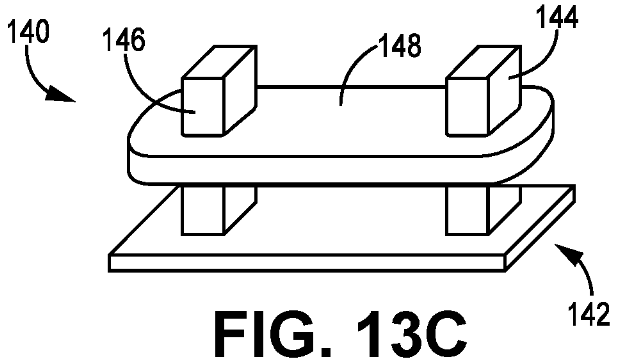
FIG. 13C is a schematic perspective view of the exemplary well of FIG. 13A in the relaxation phase, according to one embodiment.
Figure 13D:
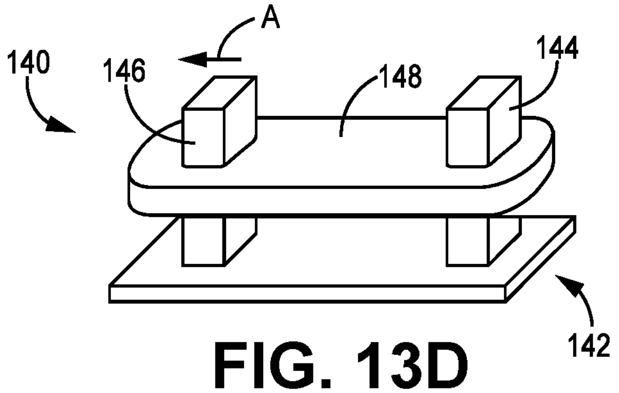
FIG. 13D is a schematic perspective view of the exemplary well of FIG. 13A in the lengthening phase, according to one embodiment.

This system 140 operates in a fashion similar to the systems 10, 80 discussed above by replicating the full cardiac cycle for the tissue constructs 148 disposed within the well 142, in this case via electrical actuation instead of fluidic or electromagnetic actuation. That is, by appropriately controlling the electrical and contractile forces via the controller 18 (as shown in FIGS. 1A and 1B with respect to system 10), the dynamic force-length relationship can be controlled for each construct 148 in each well 142 to represent the pressure-volume mechanical relationship of the heart in vivo (as depicted graphically in FIG. 4, which is also discussed above). More specifically, as shown in FIG. 13A (which replicates the contraction phase), the controller (such as controller 18) can cause electrical stimulation of the tissue 148 in each well 142 (as represented by the lightning bolt symbol 150) to drive tissue force generation. In one embodiment, the electrical stimulation is provided by electrodes (not shown) similar to electrodes 70A, 70B or 98A, 98B. In other words, the stimulation causes the tissue 148 to contract while the actuable pillar 146 is actuated to prevent tissue deformation by moving away from the tissue 148. Next, as depicted in FIG. 13B (which replicates the shortening phase), the electrical energy is removed from the actuable pillar 146 while maintaining the electrical stimulation 150 of the tissue 148, thereby allowing the pillar 146 to move back to its resting position, which enables shortening of the tissue 148 by the muscle contractile forces. At this point, as depicted in FIG. 13C (which replicates the isometric relaxation phase), the actuable pillar 146 holds the tissue 148 in place while the muscle relaxes. Finally, as shown in FIG. 13D (which replicates the lengthening phase), the actuable pillar 146 is once again actuated to move away from the tissue 148, which stretches the tissue 148 back out.

In alternative embodiments, the system 140 can also be used for other purposes. For example, in one exemplary implementation, the controller 18 can be used to actuate the electrical actuation system to perform multiplex mechanical property characterization tests by tracking tissue deformation under known forces (e.g., stiffness moduli from stress-strain plots). As noted above, an exemplary graphical summary of such tests is depicted in FIG. 6.

The various system embodiments herein provide much more reliable in vitro screening tools in comparison to known technologies by more accurately recreating the mechanical energetics of cells as they would naturally experience in the body.

Figure 5:
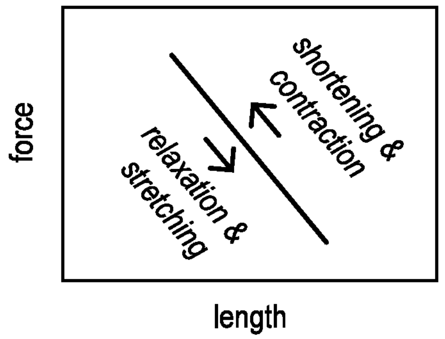
FIG. 5 is a graphical representation of the energy transfer by cardio tissue into the local attachments of known testing platforms.

In contrast, the known platforms fail to subject the tissues to the mechanical constraints experienced by myocardial cells in the body. Specifically, the known systems do not allow the micro-tissue system to perform 'active' energetic work on their environment; rather, as discussed above, the beating micro-tissues simply transfer energy into their local attachments, which immediately transfer the same energy back into the micro-tissues. This dynamic is replicated graphically in FIG. 5. This shortcoming can hinder the relevance of those platforms to mechanical disease conditions such as heart attacks, hypertension, and valve disease. Cells are highly sensitive to their mechanical, energetic context. Therefore, the known systems are limited in their screening accuracy as they do not provide an appropriate mechanical environment. In contrast, the various embodiments disclosed or contemplated herein do.

Further, the various system implementations herein are a primary measurement of function that is exactly analogous to cardiac function in vivo (specifically, stroke volume and cardiac output). This functional readout can make the screening tool implementations herein more interpretable and a better predictor compared to the known technologies. Thus, by subjecting tissues to a full mechanical loop, the system embodiments disclosed or contemplated herein provide key advantages over known approaches: (1) physiologically faithful mechanical environment, improving success of therapy screens, (2) physiologically relevant output metrics, communicating direct clinical translation, and (3) dynamic mechanical environment, providing versatility in desired testing conditions (e.g., normal vs. pressure-overload vs. volume-overload mechanics).

The various in vitro cardiac tissue culture platform embodiments herein may be used in at least 4 applications: (1) therapy screening platform for pharmaceutical and medical device companies (the platform could be used to test therapy targets, dosages, regimens, combinations, etc. in vitro prior to preclinical animal testing), (2) clinical testing platform for physicians and hospitals (the platform could be used test patients' own cells as a lab-test for improved risk stratification, disease diagnosis, and therapy selection), (3) experimental platform for researchers (the platform could be used for basic biomedical research studies to investigate cardiac tissue behavior), and/or (4) tissue maturation platform for regenerative medicine companies (the platform could be used to enhance their cardiac tissue formation procedures).

While the various systems described above are separate implementations, any of the individual components, mechanisms, or devices, and related features and functionality, within the various system embodiments described in detail above can be incorporated into any of the other system embodiments herein.

The term "about," as used herein, refers to variation in the numerical quantity that can occur, for example, through typical measuring techniques and equipment, with respect to any quantifiable variable, including, but not limited to, mass, volume, time, distance, wave length, frequency, voltage, current, and electromagnetic field. Further, there is certain inadvertent error and variation in the real world that is likely through differences in the manufacture, source, or precision of the components used to make the various components or carry out the methods and the like. The term "about" also encompasses these variations. The term "about" can include any variation of 5% or 10%, or any amount—including any integer—between 0% and 10%. Further, whether or not modified by the term "about," the claims include equivalents to the quantities or amounts.

Numeric ranges recited within the specification are inclusive of the numbers defining the range and include each integer within the defined range. Throughout this disclosure, various aspects of this disclosure are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾ This applies regardless of the breadth of the range.

Although the various embodiments have been described with reference to preferred implementations, persons skilled in the art will recognize that changes may be made in form and detail without departing from the spirit and scope thereof.

What is claimed is:

1. A cardio tissue testing system comprising:

(a) a controller;

(b) an actuator comprising an electromagnet, wherein the actuator is operably coupled to the controller;

(c) a plurality of microwells, wherein each microwell comprises a chamber operably coupled to the actuator and sized to receive a cardio tissue construct;

(d) a stationary tissue attachment structure disposed within the chamber at a first end of the chamber; and (e) an actuable tissue attachment structure disposed within the chamber at a second end of the chamber, the actuable tissue attachment structure comprising an untensioned slidable piston and a magnet attached to the slidable piston, wherein the slidable piston is slidable along a length of the chamber.

2. The cardio tissue testing system of claim 1, wherein the slidable piston comprises a piston body and a body attachment structure.

3. The cardio tissue testing system of claim 1, wherein the slidable piston is actuable by a magnetic field being applied to the magnet.

4. The cardio tissue testing system of claim 3, wherein the magnetic field is produced by the electromagnet.

5. The cardio tissue testing system of claim 1, wherein the slidable piston comprises a piston body and a body attachment structure configured to affix a cardio tissue construct.

6. The cardio tissue testing system of claim 5, wherein the body attachment structure is positioned to engage an end of the cardio tissue construct opposite the stationary tissue attachment structure.

7. The cardio tissue testing system of claim 1, wherein the slidable piston is configured to move away from and toward the stationary tissue attachment structure to cyclically stretch a cardio tissue construct disposed in the chamber.

8. The cardio tissue testing system of claim 1, wherein the slidable piston is guided for linear sliding along a longitudinal axis of the chamber.

9. The cardio tissue testing system of claim 1, wherein the chamber is sized and shaped to maintain the cardio tissue construct aligned along an axis between the stationary tissue attachment structure and the actuable tissue attachment structure.

10. A cardio tissue testing system comprising:

(a) a controller;

(b) an actuator operably coupled to the controller, wherein the actuator comprises an electromagnet;

(c) a culture plate operably coupled to the actuator, the culture plate comprising a plurality of microwells, each microwell comprising:

(i) a chamber sized to receive a cardio tissue construct;

(ii) a stationary tissue attachment structure disposed at a first end of the chamber; and (iii) an actuable tissue attachment structure comprising a slidable piston and a magnet attached to the slidable piston, wherein the slidable piston is disposed within and at a second end of the chamber, wherein the slidable piston is actuable to slide away from and toward the stationary tissue attachment structure within the microwell;

(d) an electrical power source operably coupled to the controller, wherein the electrical power source is operably coupled to electrodes associated with the culture plate; and (e) a camera operably coupled to the controller, wherein the camera is positioned to be capable of capturing images of at least one of the microwells.

11. The cardio tissue testing system of claim 10, wherein the actuable tissue attachment structure further comprises a body attachment structure configured to affix the cardio tissue construct.

12. The cardio tissue testing system of claim 11, wherein the body attachment structure is positioned to engage an end of the cardio tissue construct opposite the stationary tissue attachment structure.

13. The cardio tissue testing system of claim 10, wherein the slidable piston is configured to move away from and toward the stationary tissue attachment structure to cyclically stretch the cardio tissue construct disposed in the chamber.

14. The cardio tissue testing system of claim 10, wherein the slidable piston is guided for linear sliding along a longitudinal axis of the chamber.

15. The cardio tissue testing system of claim 10, wherein the chamber is sized and shaped to maintain the cardio tissue construct aligned along an axis between the stationary tissue attachment structure and the actuable tissue attachment structure.

16. A cardio tissue testing system comprising:

(a) a controller;

(b) an actuator operably coupled to the controller, wherein the actuator comprises an electromagnet;

(c) a culture plate operably coupled to the actuator, the culture plate comprising a plurality of microwells, each microwell comprising:

(i) a chamber sized to receive a cardio tissue construct;

(ii) a stationary tissue attachment structure disposed within the chamber at a first end of the chamber; and (iii) an untensioned slidable piston and a magnet attached thereto, wherein the slidable piston is disposed within the chamber at a second end of the chamber, wherein the slidable piston is slidable along a length of the chamber; and (d) an electrical power source operably coupled to the controller, wherein the electrical power source is operably coupled to electrodes associated with the culture plate.

17. The cardio tissue testing system of claim 16, wherein the slidable piston further comprises a body attachment structure configured to affix the cardio tissue construct.

18. The cardio tissue testing system of claim 17, wherein the body attachment structure is positioned to engage an end of the cardio tissue construct opposite the stationary tissue attachment structure.

19. The cardio tissue testing system of claim 16, wherein the slidable piston is configured to move away from and toward the stationary tissue attachment structure to cyclically stretch the cardio tissue construct disposed in the chamber.

20. The cardio tissue testing system of claim 16, wherein the slidable piston is guided for linear sliding along a longitudinal axis of the chamber.

* * * * *